United States Patent
Goldman et al.

(10) Patent No.: US 9,278,894 B2
(45) Date of Patent: Mar. 8, 2016

(54) PROCESS FOR ALKANE OLIGOMERIZATION

(75) Inventors: Alan Stuart Goldman, Highland, NJ (US); Robert Timothy Stibrany, Long Valley, NJ (US); William L. Schinski, San Ramon, CA (US)

(73) Assignees: Chevron U.S.A. Inc., San Ramon, CA (US); Rutgers, The State University of New Jersey, New Brunswick, NJ (US)

( * ) Notice: Subject to any disclaimer, the term of this patent is extended or adjusted under 35 U.S.C. 154(b) by 719 days.

(21) Appl. No.: 13/612,572

(22) Filed: Sep. 12, 2012

(65) Prior Publication Data

US 2013/0090503 A1    Apr. 11, 2013

Related U.S. Application Data

(60) Provisional application No. 61/533,982, filed on Sep. 13, 2011.

(51) Int. Cl.
| | |
|---|---|
| *C07C 2/74* | (2006.01) |
| *C07C 2/32* | (2006.01) |
| *C07C 5/333* | (2006.01) |

(52) U.S. Cl.
CPC ... *C07C 2/74* (2013.01); *C07C 2/32* (2013.01); *C07C 5/3337* (2013.01); *C07C 2531/22* (2013.01); *C07C 2531/28* (2013.01)

(58) Field of Classification Search
None
See application file for complete search history.

(56) References Cited

U.S. PATENT DOCUMENTS

| | | | |
|---|---|---|---|
| 6,689,928 B2* | 2/2004 | Stibrany et al. | 585/511 |
| 6,982,305 B2 | 1/2006 | Nagy | |
| 2004/0181104 A1 | 9/2004 | Yeh et al. | |
| 2010/0236984 A1 | 9/2010 | Brookhart et al. | |

OTHER PUBLICATIONS

R. Ahuja, S. Kundu, A. Goldman, M. Brookhart, B.. Vicentec and S. Scott. "Catalytic ring expansion, contraction, and metathesis-polymerization of cycloalkanes". Chem. Commun., 2008, 253-255.*
S. Oakley, M. Coogan, and R. Arthur. "Synthesis of Bis(imino)aryl Iridium Pincer Complexes and Demonstration of Catalytic Hydrogen-Transfer Activity". Organometallics, 2007, 26, 2285-2290.*
Catalytic Alkane Metathesis by Tandem Alkane Dehydrogenation—Olefin Metathesis A. Goldman, A. Roy, Z. Huang, R. Ahuja, W. Schinski, M. Brookhart. Science, vol. 312, Apr. 14, 2006.*
International Search Report and Written Opinion dated Nov. 21, 2012, issued in the corresponding PCT Application No. PCT/US12/55240, 8 pages.

* cited by examiner

*Primary Examiner* — In Suk Bullock
*Assistant Examiner* — Ali Z Fadhel
(74) *Attorney, Agent, or Firm* — E. Joseph Gess; Melissa M. Hayworth

(57) ABSTRACT

Provided is a process for preparing oligomers from an alkane. The process comprises (a) contacting an alkane under dehydrogenation conditions in the presence of a dehydrogenation catalyst such as an iridium catalyst complex comprising iridium complexed with a benzimidiazolyl-containing ligand to form olefins, and (b) contacting the olefins prepared in step (a) under oligomerization conditions with an oligomerization catalyst such as a nickel, platinum or palladium metal catalyst complex comprising the metal complexed with a nitrogen containing bi- or tridentate ligand to prepare oligomers of the olefins, and hydrogenating the olefin oligomers. In one embodiment, the ligands of the catalyst complexes in step (a) and step (b) can be the same.

25 Claims, 1 Drawing Sheet

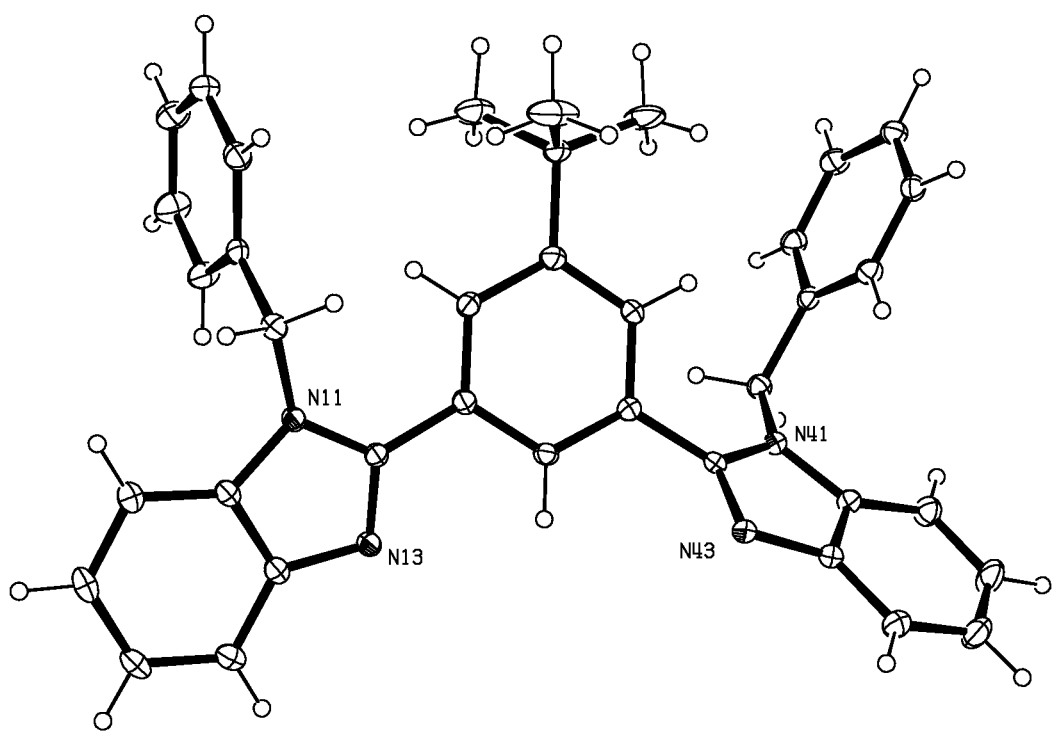

PROCESS FOR ALKANE OLIGOMERIZATION

CROSS-REFERENCE TO RELATED APPLICATIONS

This application claims benefit of U.S. Provisional Application No. 61/533,982 filed Sep. 13, 2011, entitled "PROCESS FOR ALKANE OLIGOMERIZATION", the contents of which are incorporated herein by reference in their entirety.

BACKGROUND OF THE INVENTION

1. Field of the Invention

Provided is a novel process for preparing oligomeric alkanes. More specifically, an integrated process is provided where the alkanes are first dehydrogenated to create olefins, and then the olefins are oligomerized and hydrogenated to make the oligomeric alkanes. Transition metal catalyst complexes can be used in the integrated process.

2. Description of the Related Art

Olefins can be generated by direct dehydrogenation of alkanes with the removal of hydrogen gas or by the use of an acceptor such as ethylene to generate ethane. The chemical industry uses olefins as intermediates in a variety of processes. The largest chemical use is linear α-olefins in the formation of polyolefins such as ethylene-1-octene copolymers. Also and most importantly, low carbon number olefins have the potential to be converted into higher carbon number molecules that would be suitable for fuels, particularly, diesel. Other products formed from olefins include surfactants, lubricants, and plasticizers.

Iridium complexes as catalysts are known. During the 1980s, it was discovered that certain iridium complexes are capable of catalytically dehydrogenating alkanes to alkenes under exceptionally mild thermal (i.e., less than 160° C.) or even photolytic conditions (see, e.g., *J. Am. Chem. Soc.* 104 (1982) 107; 109 (1987) 8025; *J. Chem. Soc., Chem. Commun.* (1985) 1829). For a more recent example, see *Organometallics* 15 (1996) 1532.

In recent years, the chemical industry has employed the use of organometallic catalysts to produce polymers. While many advances in organometallic catalyst technology have been made, researchers continue to seek superior catalyst compositions. In fact, very recently, novel late transition organometallic catalysts have been discovered which are very effectively used in polymerization processes. More specifically, U.S. Pat. No. 6,037,297 to Stibrany et al., herein incorporated by reference, details group IB (Cu, Ag and Au) containing catalyst compositions that are useful in polymerization processes.

Organometallic catalyst technology is also a viable tool in oligomerization processes which produce linear α-olefins for use as feedstock in various other processes. However, one problem often encountered when using many of these catalyst systems is the propensity to produce α-olefins with very low selectivity (i.e., a Schulz-Flory type distribution with high k values). For instance, many of the linear α-olefins made today utilize a neutral nickel (II) catalyst having a planar geometry and containing bidentate monoanionic ligands. While these planar nickel (II) catalysts do produce linear α-olefins, these catalysis systems exhibit a Schulz-Flory type of distribution over a very wide range (i.e., $C_4$-$C_{30+}$).

To address the Schulz-Flory distribution problem, chromium metal based catalysts have become popular for use in certain oligomerization processes. More precisely, chromium complexes have been used to oligomerize ethylene in order to form linear α-olefins with improved distributions. In fact, there has been a report of a specific chromium catalyst which selectively trimerizes ethylene to 1-hexene. These techniques employ the use of a chromium compound in conjunction with aluminoxane along with one of a variety of compounds such as nitrites, amines and ethers. Unfortunately, while these techniques have been able to selectively produce α-olefins, polymer is formed as a co-product. Of course, when polymer is co-produced, the yield of desirable product decreases accordingly. Also, as a practical matter, polymer build-up in the reaction vessel can severely hamper production efficiency thereby limiting the commercial use of such processes.

As discussed above, the organometallic catalyst technology now being used to produce α-olefins has two major disadvantages. First, many of the organometallic catalysts produce α-olefins with a Schulz-Flory type distribution. Unfortunately, this Schulz-Flory type distribution is not ideal when short chain α-olefins are desired—in other words, the selectivity is not good enough to maintain efficient processes. Because α-olefins are used as intermediates for specific products, α-olefins with certain chain lengths are desired. For instance, the following are examples of α-olefin chain lengths that would be desirable as feeds for certain product types: $C_4$ to $C_8$ for comonomer in ethylene polymerization; $C_{10}$ for lube quality poly-α-olefins; and $C_{12}$ to $C_{26}$ for surfactant products. Thus, considerable inefficiency and waste is present when significant amounts of α-olefins are produced having chain lengths outside of the range required for production of a particular chemical. Second, while some of the current organo-metallic catalysts may improve selectivity, most also produce polymer co-product. This lowers the yield of desired product and can also accumulate in the reaction vessel—both of which make commercial use less attractive and inefficient. Hence, there is still a need for improving the selectively and efficiency of linear α-olefin production.

U.S. Pat. No. 6,689,928 describes transition metal complexes and the preparation of oligomers using the complexes as catalysts. The starting material is an olefin, and overcomes the problems described above.

Improvements in the selectivity and efficiency of preparing oligomers, particularly alkane oligomers, are still needed. Processes which can improve the overall cost and economics of preparing oligomers would be of great benefit to the industry.

SUMMARY OF THE INVENTION

Provided is a process for preparing oligomers from an alkane, comprising (a) contacting an alkane under dehydrogenation conditions in the presence of a dehydrogenation catalyst, e.g., an iridium catalyst complex comprising iridium complexed with a benzimidiazolyl-containing ligand, to form olefins, and (b) contacting the olefins prepared in step (a) under oligomerization conditions in the presence of an oligomerization catalyst, e.g., a nickel, platinum or palladium metal catalyst complex comprising the metal complexed with a nitrogen containing bi- or tridentate ligand, to prepare oligomers of the olefins, followed by hydrogenation of the coupled olefinic products. All of the reactions take place in a single reactor, with both the dehydrogenation catalyst and oligomerization catalyst present. The resulting product, after hydrogenation, is an oligomeric alkane.

In one embodiment, the dehydrogenation catalyst of step (a) is an iridium complex of the formula $LMX(X')_n$, where n=0, 1 or 2, X and X' are moieties which can be eliminated from the metal center to generate a catalytically active fragment LM, M is iridium, and L is a benzimidazolyl-containing ligand.

In one embodiment, the oligomerization catalyst of step (b) is a metal catalyst complex of the formula $LMX(X')_n$, where n=0, 1 or 2, X and X' are moieties into which a monomer can insert, M is selected from the group consisting of nickel, platinum and palladium, and L is a nitrogen containing bi- or tridentate ligand.

Among other factors, it has been discovered that by using a dehydrogenation catalyst such as the particular iridium catalyst complex described above, and an oligomerization catalyst, such as the particular nickel, palladium or platinum metal catalyst complex described above, an efficient, integrated process for preparing oligomers, and in particular alkane oligomers, is achieved. The process is practiced in the same reactor with both catalysts present. In the same reactor, the reactions of dehydrogenation and oligomerization will begin to occur simultaneously, as will the hydrogenation reaction of the olefin oligomers to the alkane oligomers. The oligomerization reaction and hydrogenation reaction will actually help drive the overall reaction by using the products of the various reactions. In one embodiment, the ligands for the iridium catalyst complex and the nickel, palladium or platinum metal complex, are the same.

BRIEF DESCRIPTION OF THE FIGURES OF THE DRAWING

The FIGURE shows one embodiment of the crystal structure of 2,2'-(5-tert-butyl-1,3-phenylene)bis(1-benzylbenzimidazol-2-yl).

DETAILED DESCRIPTION OF THE INVENTION

The present invention provides a novel oligomerization method which prepares oligomers from an alkane. The method involves the dehydrogenation of an alkane to prepare olefins, subsequent oligomerization of the olefins, and then hydrogenation to give the alkane. In one embodiment, the catalysts used in each step are specific transition metal catalyst complexes.

The alkane starting materials can include straight and branched-chain compounds having from about 1-20 carbon atoms, such as methane, ethane, propane, n-butane, isobutane, n-pentane, n-hexane, 2-methylpentane, 3-methylpentane, heptane, 2-methylheptane, 3-methylheptane, octane, dodecane and the like. In one embodiment, the alkane has from 4-20 carbons. In another embodiment, the alkane is a $C_{12}$ alkane or higher.

The alkane reactant can also be a cycloalkane, where the term "cycloalkane" as used herein should be understood to include macrocyclic cycloalkanes having a carbon ring of 8 or more and up to 25 members and simple cycloalkanes having a carbon ring of less than 8 members but greater than 4 members e.g., cyclopentane, cyclohexane. Typically, the cycloalkane is a $C_5$ to $C_{20}$ membered ring.

Suitable cycloalkanes for use in the process described herein include, for example, cyclopentane, cyclohexane, cycloheptane, cyclooctane, cyclononane, cyclodecane, cycloundecane, cyclododecane, cyclotridecane, cyclotetradecane, cyclopentadecane, cyclohexadecane, cyclooctadecane, cyclononadecane, cycloicosane, cyclodocosane or cyclotetracosane.

These alkane compounds, if desired, may be substituted with various moieties, although care should be taken to exclude substituents which will adversely affect the activity of the catalyst.

The catalyst used in the dehydrogenation of the alkane can be any suitable dehydrogenation catalyst, such as a ruthenium catalyst. In one embodiment, the catalyst is an iridium catalyst complex. In a specific embodiment, the iridium is coordinated with a bi- or tridentate ligand, and in a specific embodiment, a benzimidazolyl-containing ligand.

Iridium complexed with a benzimidazolyl-containing ligand is unique. It has been found that changing the metal within the same group (column) of the periodic table, for example to rhodium, changes the bond strength which then adversely affects the ability of the catalyst to dehydrogenate the alkane. Changing the metal to another group, for example to osmium or platinum, alters the electronic configuration of the metal which would potentially require altering the ligand to accommodate greater or fewer valence electrons which would of course alter the catalytic activity. Thus, the specific Ir(NCN) catalyst as described herein is unique.

In a specific embodiment, the iridium catalyst complex is of the formula $LMX(X')_n$ where n=0, 1 or 2, X and X' are independently selected from the group consisting of halides, hydride, triflate, acetates, borates, $C_1$ through $C_{12}$ alley, $C_1$ through $C_{12}$ alkoxy, $C_3$ through $C_{12}$ cycloalkyl, $C_3$ through $C_{12}$ cycloalkoxy, $C_6$ through $C_{14}$ aryl, $C_7$ through $C_{17}$ aralkyl, olefins including diolefins, and any other moiety which can be eliminated from the metal center to generate a catalytically active LM fragment. M is iridium. L is a nitrogen-containing ligand having two or more nitrogen atoms. In one embodiment, L has the formula:

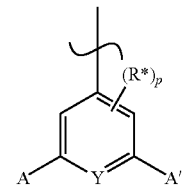

wherein A and A' are independently selected from the group consisting of:

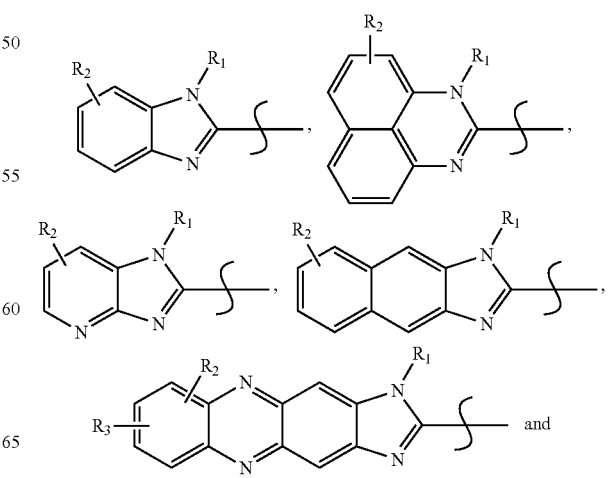

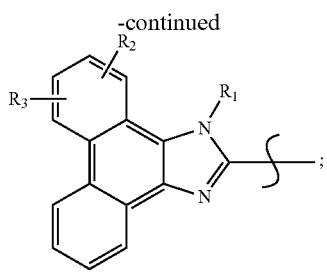

R₁, R₂, R₃ and R* are independently selected from the group consisting of halide, hydride, triflate, acetate, borate, $C_1$ through $C_{12}$ alky, $C_1$ through $C_{12}$ alkoxy, $C_3$ through $C_{12}$ cycloalkyl, $C_3$ through $C_{12}$ cycloalkoxy, $C_6$ through $C_{14}$ aryl, $C_7$ through $C_{17}$ aralkyl and olefins;

and Y is selected from the group consisting of C—H, C—Cl, C—Br, C—I, N, P, C—OR₄, wherein R₄ is hydrogen, an optionally substituted acyl group, e.g. acetyl or trifluoroacetyl, or a substituted or unsubstituted alkylsulfonyl group, e.g. methylsulfonyl or trifluoromethylsulfonyl and other leaving group; and p=0,1 or 2.

The nitrogen-containing ligands can be synthesized using techniques well known to those skilled in the art. See, for example, U.S. Pat. Nos. 6,037,297 and 6,689,928, the foregoing documents being specifically incorporated herein by reference in their entirety. In general, the novel iridium catalyst complex can be synthesized by reacting complexing Ir salts with the ligands. This can be accomplished, for example, by dissolving the Ir salt in a solvent, and then adding the ligand. The mixture is then refluxed and cooled.

The iridium catalyst complex can also be combined with an activating cocatalyst. The activating cocatalyst can be selected from the group consisting of alkylalumoxanes, aluminum alkyls, aluminum halides, alkyl aluminum halides, Lewis acids such as tris(pentafluorophenyl)borane, alkylating agents, hydrides such as lithium hydride, reducing agents such as Na/K amalgam, and mixtures thereof. The preferred ratio of metal complex to activating cocatalyst is from 1:10⁻² to 1:10⁶.

In general, the dehydrogenation reaction can be run under conventional dehydrogenation reaction conditions, as long as they are also appropriate for the concurrently run oligomerization. Generally, the reaction can be run at temperatures less than 300° C., even less than 200° C., and in one embodiment, from 150° C. to 250° C. The pressure is adjusted accordingly, and can vary greatly, e.g., from 5 to 30,000 psig. The important aspect is that the conditions are selected to enhance all of the reactions with the catalysts chosen.

The dehydrogenation catalyst may be supported. The support material maybe a porous material, which includes, but is not limited to, inorganic oxides, zeolites, and inorganic chlorides. The support may also be resinous materials such as polystyrene, polyolefin, and other polymeric materials. These catalyst can be physiosorbed on the support or chemically bonded to the support.

The catalyst used for the oligomerization can be any suitable oligomerization catalyst, e.g., a zirconium, hafnium or chromium catalyst. In a specific embodiment, the oligomerization catalyst is also of the formula LMX(X')ₙ, where n=0, 1 or 2, X and X' are independently selected from the group consisting of halides, hydride, triflate, acetates, borates, $C_1$ through $C_{12}$ alky, $C_1$ through $C_{12}$ alkoxy, $C_3$ through $C_{12}$ cycloalkyl, $C_3$ through $C_{12}$ cycloalkoxy, C6 through C14 aryl, C7 through C17 aralkyl, olefins including diolefins, and any other moiety into which a monomer can insert. M is selected from the group consisting of nickel, palladium, and platinum. L is a nitrogen-containing ligand having two or more nitrogen atoms. In a preferred embodiment L has the formula:

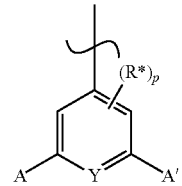

wherein A and A' are independently selected from the group consisting of:

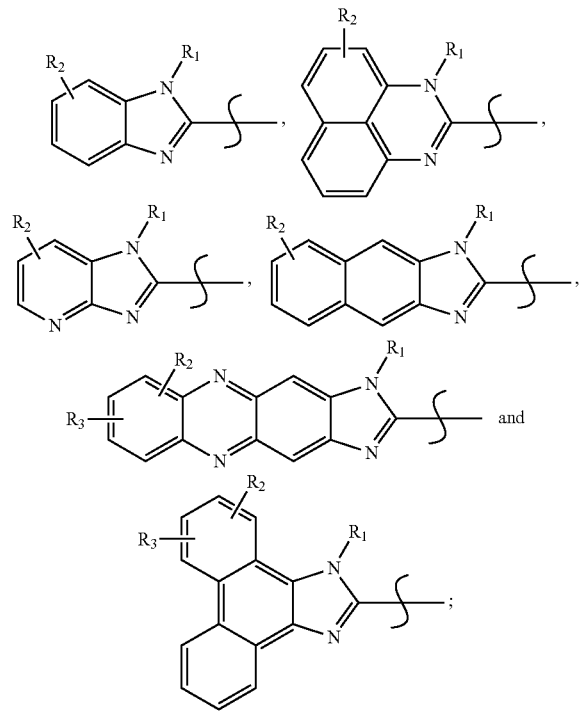

R₁, R₂, R₃ and R* are independently selected from the group consisting of halide, hydride, triflate, acetate, borate, $C_1$ through $C_{12}$ alky, $C_1$ through $C_{12}$ alkoxy, $C_3$ through $C_{12}$ cycloalkyl, $C_3$ through $C_{12}$ cycloalkoxy, $C_6$ through $C_{14}$ aryl, $C_7$ through $C_{17}$ aralkyl and olefins;

and Y is selected from the group consisting of C—H, C—Cl, C—Br, C—I, N, P, C—OR₄, wherein R₄ is hydrogen, an optionally substituted acyl group, e.g. acetyl or trifluoroacetyl, or a substituted or unsubstituted alkylsulfonyl group, e.g. methylsulfonyl or trifluoromethylsulfonyl and other leaving group; and p=0,1 or 2.

The nitrogen-containing ligands for the oligomerization catalyst can be synthesized using techniques well known to those skilled in the art. See, for example, U.S. Pat. Nos. 6,037,297 and 6,689,928, foregoing documents being specifically incorporated herein by reference in their entirety. In general, the novel metal catalyst complex can be synthesized by reacting complexing metal salts with the ligands. This can be accomplished, for example, by dissolving the metal salt in a solvent, and then adding the ligand. The mixture is then refluxed and cooled.

The oligomerization catalyst can also be combined with an activating cocatalyst. The activating cocatalyst is selected from the group consisting of alkylalumoxanes, aluminum alkyls, aluminum halides, alkyl aluminum halides, Lewis acids such as tris(pentafluorophenyl)borane, alkylating agents, hydrides such as lithium hydride, reducing agents such as Na/K amalgam, and mixtures thereof. The preferred ratio of metal complex to activating cocatalyst is from $1:10^{-2}$ to $1:10^6$.

The oligomerization catalyst can also be supported. The support material maybe a porous material, which includes, but is not limited to, inorganic oxides, zeolites, and inorganic chlorides. The support may also be resinous materials such as polystyrene, polyolefin, and other polymeric materials. These catalyst maybe physiosorbed on the support or chemically bonded to the support.

Generally, oligomerization may be accomplished utilizing temperatures and pressures used in the prior art. The temperatures and pressures discussed previously are appropriate. The important aspect is that the conditions are selected to best enhance all of the reactions occurring in the reactor with the chosen catalysts.

Once the olefins have been oligomerized, the olefin oligomers are hydrogenated to provide alkane oligomers, i.e., alkanes of higher molecular weight. Hydrogen is present in the reactor from the dehydrogenation, and the catalysts present can also act as catalysts for the hydrogenation reaction. By removing the olefin oligomer products and the hydrogen created by the dehydrogenation reaction, the overall reaction of dehydrogenation to olefins to oligomers is driven to completion.

All the reactions in the reactor can take place in a solvent, neat (e.g., no solvent and liquid condensed olefin), or in gas phase (e.g., olefin in gas phase and catalyst in solid phase). When the reactions are conducted in a solvent phase, suitable solvents include, but are not limited to propane, butane, pentane, hexane, toluene, olefins, carbon dioxide, ionic liquids and mixtures thereof. In one embodiment, toluene is used effectively as the solvent.

In one embodiment, the ligands for the dehydrogenation Ir catalyst complex and the oligomerization Ni, Pd or Pt metal catalyst complex are the same. The distinct advantages of this are economic and practical. Economically, catalyst synthesis costs would be less if the same ligand is used. From a practical standpoint, using the same ligand eliminates the problems of ligand exchange, thereby leading to a more effective overall process. Using the same ligands even further enhances the efficiency and effectiveness of the present integrated process. In one embodiment, the ligands for the Ir dehydrogenation catalyst and the Ni, Pd or Pt catalyst complexes are benzimidazolyl-containing ligands.

The following examples are provided to further illustrate the present invention, but are not meant to be limiting.

Example 1

Preparation of 2,2'-(1,3-phenylene)bis(1-propylbenzimidazol-2-yl)

In a 50 mL Erlenmeyer flask, 450 mg of 2,2'-(2-bromo-1,3-phenylene)bis(1-hydrobenzimidazol-2-yl) (1.45 mmol) was added. Then 15 mL of N,N-dimethylformamide was added followed by the addition of 300 μL of 1-iodopropane (3.13 mmol). Then 800 mg of powdered NaOH was added to the mixture. After 0.5 hours the mixture had turned light brown. The flask was stoppered and left to stir overnight at room temperature. The reaction was then quenched with water. The reaction mixture was then extracted with about 40 mL of ethyl acetate and 60 mL of water. The pale-brown organic phase was separated and placed in a beaker to evaporate. After evaporation of the volatiles, a pale-brown solid was obtained. $C_{26}H_{25}N_4$, fw=393.50. Mp: 168° C. (sft) 195° C. (melt). $^1$H NMR (300 MHz, CDCl$_3$): δ 7.81 (d, J=6.9 Hz, 2H), 7.65 (d, J=6.9 Hz, 2H), 7.58 (m, 1H), 7.31 (m, 6H), 3.99 (br m, 4H), 1.71 (q, J=6.4 Hz, 4H), 0.82 (t, J=6.4 Hz, 6H). $^{13}$C NMR (100 MHz, CDCl$_3$): δ 151.9, 145.1, 143.1, 134.8, 134.1, 134.0, 123.3, 122.7, 120.5, 110.6, 46.6, 23.1, 11.5. $R_f$=0.47 (ethyl acetate/silica). X-ray: a=25.261 (7) Å, b=10.469 (3) Å, c=8.527 (2) Å, α=90°, β=90°, γ=90°, V=2255.0 (10).

Example 2

Preparation of 2-chloro-5-tert-butyl-1,3-dimethylbenzene

In a 500 mL round bottom flask 4.50 g of 2-bromo-5-tert-butyl-1,3-dimethylbenzene (18.6 mmol) and 9.50 g of NiCl$_2$.6 H$_2$O (40.0 mmol) were added. Then 30 mL of N,N-dimethylformamide was added to the flask, giving a blue-green solution. The flask was fitted with a condenser and was left to reflux with stirring. After 0.5 hours the solution was dark blue. After refluxing for 5 days the mixture was cooled to rt and then diluted with 25 mL of 2 M HCl. The aqueous phase was extracted with 40 mL of ethyl acetate. The volatiles were removed from the extract by evaporation to give a white solid. (91% conversion to the title product) All of the solids were dissolved in 25 mL of N,N-dimethylformamide and the solution was placed in a 125 mL round bottom flask. Then 5.1 g of NiCl$_2$·6 H$_2$O (21.5 mmol) was added to the flask. The flask was fitted with a condenser and was left to reflux with stirring. After 0.5 hours the solution was dark blue. After refluxing for 5 days the mixture was cooled to rt and then diluted with 25 mL of 2 M HCl. The aqueous phase was extracted with 40 mL of ethyl acetate. The volatiles were removed from the extract by evaporation to give a white solid. $C_{12}H_{17}Cl$, fw=196.72. Yield 3.51 g, 95.6%. Mp: 39° C. (melt). $^1$H NMR (300 MHz, CDCl$_3$): δ 7.01 (s, 2H), 2.30 (s, 6H), 1.22 (s, 9H). $R_f$=0.69 (cyclohexane/silica).

Example 3

Preparation of 2-chloro-5-tert-butyl-isophthalic ccid

To a 250 mL round bottom flask 4.38 g of 2-chloro-5-tert-butyl-1,3-dimethylbenzene (22.3 mmol) was added. Then 40 mL of 1:1 v/v t-butanol/water was added to the flask. Then 8.00 g of KMnO$_4$ (50.6 mmol) was added and the mixture was refluxed for 1 hour and cooled to rt. An additional 8.00 g of KMnO$_4$ (50.6 mmol) was added and the mixture was refluxed for 4 days. The reaction mixture was then filtered hot and washed with an additional 10 mL of water. The filtrate was reduced in volume by about half by evaporation. The filtrate was then made acidic with conc. HCl. The mixture was then cooled in an ice/water bath for 0.5 hours. The precipitate was collected by filtration and was washed with 20 mL of water. The white solid was allowed to air dry. $C_{12}H_{13}ClO_4$, fw=256.68. Yield 5.38 g, 94.1%. Mp: 250° C. (soften) 264° C. (melt). $^1$H NMR (300 MHz, CD$_3$COCD$_3$): δ 7.90 (s, 2H), 1.37 (s, 9H).

Example 4

Preparation of 3,4-dimethyl-1,2-phenylene diamine

To a 125 mL round bottom flask 2.20 g of 2,3-dimethyl-6-nitro-aniline (13.2 mmol) was added. Then 15 mL of ethanol was added to the flask followed by the addition of 4 mL of 20 wt % NaOH in water. Then 2.0 g of zinc dust was added to the flask. The flask was fitted with a condenser and was left to reflux with stirring. After about 0.5 hours the mixture became very pale-brown. After refluxing for 18 hours the mixture was filtered hot to give a pale filtrate which quickly became dark red. $C_8H_{12}N_2$, fw=136.19. Yield 1.78 g, 98.7%. Mp: 60° C. (melt). $^1$H NMR (300 MHz, $CDCl_3$): δ 6.54 (s, 2H), 3.46 (br s, 2H), 3.21 (br s, 2H), 2.22 (s, 3H), 2.11 (s, 3H). $R_f$=0.68 (ethyl acetate/silica).

Example 5

Preparation of 2,2'-(5-tert-butyl-2-chloro-1,3-phenylene)bis(1-hydro-4,5-dimethylbenzimidazol-2-yl)

In a 125 mL round bottom flask 0.6128 g of 2-chloro-5-tert-butyl-isophthalic acid (2.40 mmol) and 0.650 g of 3,4-dimethyl-1,2-phenylenediamine (4.77 mmol) were added. Then 10 mL of polyphosphoric acid was added to the flask. The flask was fitted with a condenser and heated to 190-200° C. with stirring. After 2 days the mixture was cooled to about 90° C. and then made basic (pH>9) with concentrated ammonium hydroxide. The mixture was diluted with 50 mL of water. The solids were collected by filtration, washed with water, and air dried. The solids were then placed in a 125 mL round bottom flask containing 2 g of activated carbon. Then 35 mL of ethanol were added to the flask. The flask was fitted with a condenser and was left to reflux with stirring. After refluxing for 10 days the mixture was cooled to rt and then filtered. The solids were washed with an additional 10 mL of ethyl acetate. The clear filtrate was evaporated to give a pale-brown crystalline solid. $C_{28}H_{29}ClN_4$, fw=457.01. Yield 405 mg, 37.0%. Mp: 217° C. (soften) 265° C. (melt). $^1$H NMR (300 MHz, $CDCl_3$): δ 7.83 (s, 2H), 7.34 (d, J=8.4 Hz, 2H), 7.09 (d, J=7.4 Hz, 2H), 2.51 (s, 6H), 2.38 (s, 6H), 1.39 (s, 9H). $R_f$=0.11 (ethyl acetate/silica).

Example 6

Preparation of 2,2'-(5-tert-butyl-2-chloro-1,3-phenylene)bis(1-propyl-4,5-dimethylbenzimidazol-2-yl)

In a 25 mL round bottom flask, 800 mg of 2,2'-(5-tert-butyl-2-chloro-1,3-phenylene)bis(1-hydrobenzimidazol-2-yl) (1.75 mmol) was added. Then 6 mL of dimethyl sulfoxide was added slowly giving a pale yellow solution. Then 500 mg of NaH (95%) was slowly added and was allowed to stir an additional 15 min. Then 360 μL of 1-iodopropane (3.69 mmol) was added dropwise. The flask was sealed and the mixture was allowed to stir at room temperature. After 2 days the mixture was quenched with water. The reaction mixture was then extracted with about 40 mL of ethyl acetate and 40 mL of water. The organic phase was separated and reduced in volume to ca. 4 mL. The brown liquid was chromatographed on silica with ethyl acetate. The first pale yellow band was collected and taken to dryness to give a pale-yellow solid. $C_{34}H_{41}ClN_4$, fw=541.17. Yield 373 mg, 46.6% %. Mp: 221° C. (soften) 254° C. (melt). $^1$H NMR (300 MHz, $CDCl_3$): δ 7.66 (s, 2H), 7.18 (d, J=12.8 Hz, 2H), 7.15 (d, J=12.8 Hz, 2H), 4.07 (br m, 4H), 2.64 (s, 6H), 2.41 (s, 6H), 1.72 (q, J=7.1 Hz, 4H), 1.34 (s, 9H), 0.76 (t, J=7.1 Hz, 6H). $R_f$=0.81 (ethyl acetate/silica).

Example 7

Preparation of Ir[($κ^3$N,C,N) 2,2'-(5-tert-butyl-1,3-phenylene)bis(1-propyl-4,5-dimethylbenzimidazol-2-yl)]dichloride In an argon glove box 60 mg of 2,2'-(5-tert-butyl-2-chloro-1,3-phenylene)bis(1-propyl-4,5-dimethylbenzimidazol-2-yl) (0.13 mmol) was placed in a 50 mL round bottom flask. This was followed by the addition of 37 mg of $Ir_2(COD)_2Cl_2$ (0.055 mmol) and 10.0 mL of acetonitrile. The flask was sealed with a septa. The flask contained a yellow-orange solution. After stirring at room temperature for one hour the mixture became orange. After stirring at room temperature for 38 hours, the volatiles were removed under vacuum to give a yellow glass. Acetone was added to the slurry and a steel blue solution was obtained. All of the volatiles were removed under vacuum to give a steel blue glass. $C_{34}H_{41}Cl_2IrN_4$, fw=768.84. IR(KBr pellet, cm$^{-1}$) 2963 s, 2933 s, 2875 m, 2831 w, 1466 s, 1382 m, 1327 w, 1298 w, 1146 w, 896 w, 789 m, 611 w, 494 w.

Example 8

Preparation of Ir[($κ^3$N,C,N) 2,2'-(5-tert-butyl-1,3-phenylene)bis(1-propyl-4,5-dimethylbenzimidazol-2-yl)]ethylene In an Ar glovebox 10 mg of Ir[($κ^3$N,C,N) 2,2'-(5-tert-butyl-1,3-phenylene)bis(1-propyl-4,5-dimethylbenzimidazol-2-yl)]dichloride was placed in a 125 mL round bottom flask. Then about 7 mL of benzene was added to give a yellow solution. Then 30 mg of Na/K alloy was added to the flask. The flask was sealed with a septa and taken to an ethylene line where the flask was flushed with ethylene and then left under a positive pressure of 5 psig of ethylene. The yellow-orange mixture was left to stir. After stirring for 18 hours, the volatiles were removed under vacuum to give an orange solid. $^1$H NMR (400 MHz, $CDCl_3$): δ 7.69 (s, 2H), 7.14 (m, 2H), 7.08 (m, 2H), 4.69 (br m, 4H), 2.80 (s, 6H), 2.33 (s, 6H), 2.21 (s, 4H), 1.59 (m, 4H), 1.41 (s, 9H), 0.64 (m, 6H).

Example 9

Transfer Dehydrogenation

In an Ar glovebox 2.6 mg of [Ir[($κ^3$N,C,N) 2,2'-(1,3-phenylene)bis(1-propylbenzimidazol-2-yl)]hydridobromide]$_2$ was placed in a 35 mL glass pressure reactor. Then 5.0 mL of toluene was added to give a brown solution with some suspended solid. Then 2.0 mL of 1-octane was added to the reactor. The reactor was sealed and was immersed in an oil bath at 110° C. and was left to stir for 95 h. Gas Chromatograph (GC) analysis of products from 1-octane conversion: 0.41% octane, 1.2% internal octane isomers, 0.45% dienes, 0.23% trienes, 0.47% dimers.

Example 10

Acceptorless Dehydrogenation

In an Ar glovebox 4.0 mg of [Ir[($κ^3$N,C,N) 2,2'-(1,3-phenylene)bis(1-propylbenzimidazol-2-yl)]hydridobromide]$_2$ was placed in a flow through dehydrogenation apparatus. Then 6.0 mL of n-dodecane was added to give a very pale-brown solution with suspended solid. The apparatus was sealed and taken to an Ar Schlenk line. There a flow through rate of ca. 5 mL/min. was established. The condenser was connected and the reservoir was immersed in a sand bath and a gentle reflux was established. The dehydrogenation was run for 164 hrs. Gas Chromatograph (GC) analysis of products from n-dodecane conversion: 0.003% 1-dodecene, 0.012% internal dodecene isomers, 0.015% dienes.

Example 11

Preparation of 2,2'-(5-tert-butyl-1,3-phenylene)bis(1-hydrobenzimidazol-2-yl)

In a 250 mL round bottom flask 2.50 g of 5-tert-butyl-isophthalic acid (11.3 mmol) and 2.44 g of 1,2-phenylenediamine (22.6 mmol) were added. Then 8 mL of polyphosphoric acid was added to the flask. The flask was fitted with a condenser and heated to 180° C. with stirring. After 4 days the mixture was cooled to about 100° C. and then made basic (pH>9) with concentrated ammonium hydroxide. The mixture was diluted with 25 mL of water. The solids were collected by filtration, washed with water, and air dried. The solids were then placed in a 250 mL round bottom flask containing 2 g of activated carbon. Then 30 mL of ethyl acetate and 10 mL of ethanol were added to the flask. The flask was fitted with a condenser and was left to reflux with stirring. After refluxing for 18 hours the mixture was cooled to rt and then filtered. The solids were washed with an additional 10 mL of ethyl acetate. The clear filtrate was evaporated to give a pale-brown crystalline solid. $C_{24}H_{22}N_4$, fw=366.46. Yield 911 mg, 22.0%. Mp: 102° C. (soften) 209° C. (melt). $^1$H NMR (300 MHz, CDCl$_3$): δ 8.96 (s, 1H), 8.39 (s, 2H), 7.70 (br s, 4H), 7.28 (m, 4H), 3.38 (br s, 2H), 1.53 (s, 9H). $R_f$=0.65 (ethyl acetate/silica).

Example 12

Preparation of 2,2'-(5-tert-butyl-1,3-phenylene)bis(1-benzylbenzimidazol-2-yl)

In a 50 mL Erlenmeyer flask, 500 mg of 2,2'-(5-tert-butyl-1,3-phenylene)bis(1-hydrobenzimidazol-2-yl) (1.36 mmol) was added. Then 15 mL of N,N-dimethylformamide was added followed by the addition of 320 µL of benzyl chloride (2.78 mmol). Then 800 mg of powdered NaOH was added to the mixture. After 0.5 hours the mixture had turned light brown. The flask was stoppered and left to stir overnight at room temperature. The reaction was then quenched with water. The reaction mixture was then extracted with about 40 mL of ethyl acetate and 60 mL of water. The pale-brown organic phase was separated and placed in a beaker to evaporate. After evaporation of the volatiles, a pale-brown crystalline solid was obtained. $C_{38}H_{34}N_4$, fw=546.70. Mp: 140° C. (opaque) 245° C. (melt). $^1$H NMR (300 MHz, CDCl$_3$): δ 7.92 (t, J=1.3 Hz, 1H), 7.89 (d, J=7.6 Hz, 2H), 7.74 (d, J=1.5 Hz, 2H), 7.28 (m, 12H), 7.06 (dd, J=1.5 Hz, J=7.6 Hz, 4H), 5.42 (s, 4H), 1.14 (s, 9H). $^{13}$C NMR (CDCl$_3$): δ 154.0, 152.8, 143.4, 136.6, 136.3, 130.8, 129.3, 128.3, 128.0, 127.5, 126.3, 123.4, 122.9, 120.3, 110.7, 35.1, 31.1. $R_f$=0.70 (ethyl acetate/silica). X-ray: a=12.470 (6) Å, b=11.223 (5) Å, c=23.209 (11) Å, α=90°, β=104.486 (9)°, γ=90°, V=3145 (2). FIG. 1 depicts the structure of the recovered product.

Example 13

Preparation of Ni(N,N)(2,2'-(5-tert-butyl-1,3-phenylene)bis(1-benzylbenzimidazol-2-yl) Cl$_2$ In an 25 mL Erlenmeyer flask containing ca. 2 mL of methylene chloride and ca. 2 mL of ethanol, 72.5 mg of 2,2'-(5-tert-butyl-1,3-phenylene)bis(1-benzylbenzimidazol-2-yl) (0.13 mmol) and 29.1 mg of Ni(glyme)Cl$_2$ (0.13 mmol) were added, quickly giving a yellow solution. The mixture was left to stir at room temperature overnight. The mixture became a white slurry. Acetone was added to the slurry and a steel blue solution was obtained. All of the volatiles were removed under vacuum to give a steel blue glass. $C_{38}H_{34}Cl_2N_4Ni$, fw=676.30. IR(KBr pellet, cm$^{-1}$) 2962, 1453, 891, 746, 697.

Example 14

Preparation of 2,2'-(1-Bromo-4-tert-butyl-2,6-phenylene)bis(1-hydrobenzimidazol-2-yl)

To a 250 mL round bottom flask 6.397 g of 1-bromo-4-tert-butyl-2,6-isophthalic acid (21.2 mmol) and 4.595 g of 1,2-phenylenediamine (42.5 mmol) were added, followed by the addition of 8 mL of polyphosphoric acid. The flask was fitted with a condenser and was placed in a sand bath where the temperature was maintained between 180° C. and 200° C. The reaction mixture became a green mass. After heating overnight a black viscous liquid formed. The mixture was cooled to about 100° C. and then made basic (pH~10) with concentrated ammonium hydroxide. After cooling to room temperature the black solids were collected by filtration, washed with water, and air dried. All of the solids were then placed in a 250 mL round bottom flask containing 2 g of activated carbon. Then 10 mL of ethyl acetate and 40 mL of ethanol were added to the flask. The flask was fitted with a condenser and was left to reflux with stirring. After refluxing overnight the mixture was filtered hot and the solids were washed with ethanol to give a clear, very pale-yellow solution. The solvent was removed under evaporation to give an off white solid. $C_{24}H_{21}BrN_4$, fw=445.35. Yield 6.51 g, 68.8%. Mp: 190° C. (soften) 290-305 (phase) 337-338° C. (melt). $^1$H NMR (400 MHz, CD$_3$SOCD$_3$): δ 7.78 (s, 2H), 7.63 (m, 4H), 7.24 (m, 4H), 1.31 (s, 9H). IR(KBr pellet, cm$^{-1}$) 3066 m, 2064 s, 1627 m, 1452 m, 1228 m, 1100 s, 960 s, 893 m, 748 s, 617 m, 519 m. $R_f$=0.70 (ethyl acetate/silica).

Example 15

Preparation of 2,2'-(1-Bromo-5-tert-butyl-2,6-phenylene)bis(1-methylcyclohexylbenzimidazol-2-yl)

In a 250 mL Erlenmeyer flask, 2.00 g of 2,2'-(1-bromo-4-tert-butyl-2,6-phenylene)bis(1-hydrobenzimidazol-2-yl) (4.49 mmol) and 1.60 g of (bromomethyl)cyclohexane (9.03 mmol) were added. This was followed by the addition of 25 mL of N,N-dimethylformamide. Then 2.0 g of powdered NaOH was added to the mixture. The flask containing the pale yellow mixture was stoppered and left to stir at room temperature. After stirring overnight, 50 mL of water was added to the mixture. The reaction mixture was then extracted with about 35 mL of ethyl acetate. The organic phase was then washed with 50 mL of 5 wt. % sodium carbonate in water. The organic phase was then evaporated to dryness. $C_{38}H_{45}BrN_4$, fw=637.69. Mp: 96 (onset soften) 196° C. (melt). $^1$H NMR (400 MHz, CDCl$_3$): δ 7.78 (m, 2H), 7.64 (s, 1H), 7.36 (m, 2H), 7.27 (m, 4H), 7.19 (s, 1H), 3.79 (dm, 4H), 1.73 (br m, 2H), 1.54 (br m, 10H), 1.28 (s, 9H), 1.27-0.86 (br m, 10H). $^{13}$C NMR (CDCl$_3$): δ 150.8, 144.6, 143.0, 135.1, 133.3, 132.0, 125.4, 123.2, 122.6, 120.4, 110.8, 51.2, 38.2, 35.1, 31.2, 31.1, 26.3, 25.8. $R_f$=0.76 (ethyl acetate/silica).

Example 16

Preparation of Ni(N,C,N) 2,2'-(5-tert-butyl-2,6-phenylene)bis(1-methylcyclohexylbenzimidazol-2-yl) bromide In an argon glove box 114 mg of 2,2'-(1-bromo-4-tert-butyl-2,6-phenylene)bis(1-methylcyclohexylbenzimidazol- 2-yl) (0.18 mmol) was placed in a 50 mL round bottom flask. This was followed by the addition of 53 mg of Ni(COD)$_2$ (0.19 mmol) and 6.0 mL of toluene. The flask was sealed with a septa. The flask contained a pale-yellow solution with some suspended solid. After stirring at room temperature for one hour the mixture became dark green with some suspended solid. After stirring at room temperature for 38 hours, the reaction mixture contained a grey-green suspension. The volatiles were removed under vacuum to give a grey-green ferromagnetic solid powder. Acetone was added to the slurry and a steel blue solution was obtained. All of the volatiles were removed under vacuum to give a steel blue glass. $C_{38}H_{44}BrN_4Ni$, fw=696.39. IR(KBr pellet, cm$^{-1}$) 2922 s, 2850 m, 1578 s, 1533 m, 1446 s, 1364 w, 1290 w, 1171 w, 1016 w, 739 s, 624 w, 433 w.

Example 17

Preparation of Pd(N,C,N) 2,2'-(5-tert-butyl-2,6-phenylene)bis(1-propylbenzimidazol-2-yl) bromide In an argon glove box 30 mg of 2,2'-(1-bromo-4-tert-butyl-2,6-phenylene)bis(1-propylbenzimidazol-2-yl) (0.016 mmol) was placed in a 25 mL round bottom flask. This was followed by the addition of 30 mg of Pd$_2$(dba)$_3$ (0.033 mmol) and 5.0 mL of benzene. The flask was sealed with a septa. After stirring at room temperature for five minutes the mixture became dark red-purple. After stirring at room temperature for 4 days, the reaction mixture was dark green. The volatiles were removed under vacuum to give a green amorphous powder. $C_{30}H_{33}BrN_4Pd$, fw=635.93. IR(KBr pellet, cm$^{-1}$) 3057 w, 2961 m, 2873 w, 1649 s, 1577 s, 1446 m, 1339 m, 1191 m, 1099 w, 982 m, 746 s, 696 s, 527 m.

Example 18

Oligomerization

In an argon glove box 4.0 mg of Ni(N,N)(2,2'-(5-tert-butyl-1,3-phenylene)bis(1-benzylbenzimidazol-2-yl) Cl$_2$ was placed in a 15 mL glass pressure reactor. Then 1.0 mL of 1-octene, 1.5 mL of toluene, and 0.5 mL of 10% methylalumoxane in toluene were added sequentially. The mixture became pale orange with some suspended solid. The reactor was sealed and taken to an oil bath where it was immersed at 110° C. for 117 hours with stirring. The reaction was then removed from the oil bath and cooled to room temperature. The reaction was then quenched with ca. 2 mL of methanol. The sample was analyzed by GC analysis. Products (wt %) 2.17, 1-octene; 91.62, octene isomers; 6.05, octene dimers; 0.16, octene trimers. If this reaction had been combined with the reaction of Example 9, in the same reactor, alkane oligomers would have been obtained upon hydrogenation of the olefin oligomers.

Example 19

Oligomerization

In an argon glove box 4.0 mg of Ni(N,C,N) 2,2'-(5-tert-butyl-2,6-phenylene)bis(1-methylcyclohexylbenzimidazol-2-yl) bromide was placed in a 15 mL glass pressure reactor. Then 0.5 mL of 1-hexene, 2.0 mL of toluene, and 0.5 mL of 10% methylalumoxane in toluene were added sequentially. The mixture became pale orange with some suspended solid. The reactor was sealed and taken to an oil bath where it was immersed at 120° C. for 117 hours with stirring. The reaction was then removed from the oil bath and cooled to room temperature. The reaction was then quenched with ca. 2 mL of methanol. The sample was analyzed by GC analysis. Products (wt %) 16.88, 1-hexene; 78.64, hexene isomers; 4.37, hexene dimers. Combining this reaction with a reaction similar to Example 9, in the same reactor, would provide alkane oligomers upon hydrogenation of the olefin oligomers.

Example 20

Oligomerization

In an argon glove box 4.2 mg of Pd(N,C,N) 2,2'-(5-tert-butyl-2,6-phenylene)bis(1-propylbenzimidazol-2-yl) bromide was placed in a 15 mL glass pressure reactor. Then 0.5 mL of 1-hexene, 3.0 mL of toluene, and 0.5 mL of 10% methylalumoxane in toluene were added sequentially. The mixture became pale green-brown. The reactor was sealed and taken to an oil bath where it was immersed at 80° C. for 140 hours with stirring. The reaction was then removed from the oil bath and cooled to room temperature. The reaction was then quenched with ca. 2 mL of methanol. The sample was analyzed by GC analysis. Products (wt %) 87.76, 1-hexene; 11.93, hexene isomers; 0.31, hexene dimers. Combining this reaction with a reaction similar to Example 9, in the same reactor, would provide alkane oligomers upon hydrogenation of the olefin oligomers.

Various modifications and alterations of this invention will become apparent to those skilled in the art without departing from the scope and spirit of the invention. Other objects and advantages will become apparent to those skilled in the art from a review of the preceding description.

A number of patent documents and non-patent documents are cited in the foregoing specification in order to describe the state of the art to which this invention pertains. The entire disclosure of each of the cited documents is incorporated by reference herein.

Furthermore, the transitional terms "comprising", "consisting essentially of" and "consisting of", when used in the appended claims, in original and amended form, serve to indicate what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All iridium catalyst complexes and methods of use thereof that embody the present invention can, in alternate embodiments, be more specifically defined by any of the transitional terms "comprising", "consisting essentially of" and "consisting of".

That which is claimed is:

1. A process for preparing oligomers from an alkane, comprising
    (a) contacting an alkane under dehydrogenation conditions in the presence of a dehydrogenation catalyst to form olefins, wherein the dehydrogenation catalyst comprises an iridium catalyst complex comprising iridium complexed with a benzimidazolyl-containing ligand, (b) contacting the olefins prepared in step (a) under oligomerization conditions with an oligomerization catalyst to prepare oligomers of the olefins, and (c) hydrogenating the olefin oligomers, with all reactions occurring in a single reactor.

2. The process of claim 1, wherein the iridium complex is of the formula $LMX(X')_n$, where n=0, 1 or 2;

X and X' are moieties into which a monomer can insert or which can be eliminated from the metal center to generate a catalytically active fragment LM;

M is iridium; and

L is a benzimidazolyl-containing ligand.

3. The process of claim 2, wherein X and X' are independently selected from the group consisting of halides, hydride, triflate, acetates, borates, $C_1$ through $C_{12}$ alkyl, $C_1$ through $C_{12}$ alkoxy, $C_3$ through $C_{12}$ cycloalkyl, $C_3$ through $C_{12}$ cycloalkoxy, $C_6$ through $C_{14}$ aryl, $C_7$ through $C_{17}$ aralkyl and olefins.

4. The process of claim 2, wherein L has the formula:

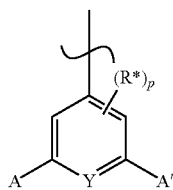

wherein A and A' are independently selected from the group consisting of:

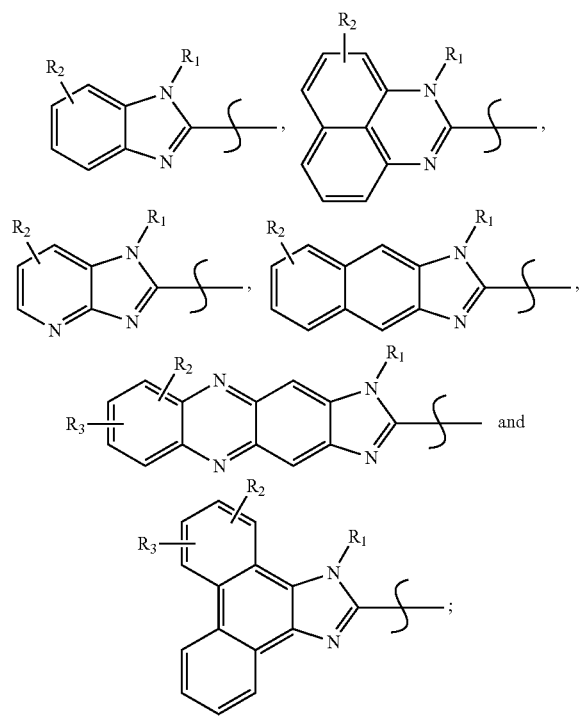

$R_1$, $R_2$, $R_3$ and R* are independently selected from the group consisting of halide, hydride, triflate, acetate, borate, $C_1$ through $C_{12}$ alky, $C_1$ through $C_{12}$ alkoxy, $C_3$ through $C_{12}$ cycloalkyl, $C_3$ through $C_{12}$ cycloalkoxy, $C_6$ through $C_{14}$ aryl, $C_7$ through $C_{17}$ aralkyl and olefins;

and Y is selected from the group consisting of C—H, C—Cl, C—Br, N, P, C—OR$_4$, wherein R$_4$ is hydrogen, an optionally substituted acyl group, a substituted or unsubstituted alkylsulfonyl group, or other leaving group; and p=0,1 or 2.

5. The process of claim 2, wherein the benzimidazolyl based ligand is 2,2'-(1,3-phenylene)bis(1-propylbenzimidazol-2-yl).

6. The process of claim 4, wherein X and X' are independently selected from the group consisting of halides, hydride, triflate, acetates, borates, $C_1$ through $C_{12}$ alky, $C_1$ through $C_{12}$ alkoxy, $C_3$ through $C_{12}$ cycloalkyl, $C_3$ through $C_{12}$ cycloalkoxy, $C_6$ through $C_{14}$ aryl, $C_7$ through $C_{17}$ aralkyl and olefins.

7. The process of claim 1, wherein the iridium is coordinated with the nitrogen atoms in the benzimidazolyl-containing ligand to form an NCN pincer ligand.

8. The process of claim 2, wherein the alkane in step (a) is contacted with a combination of the iridium catalyst complex and a co-catalyst.

9. The process of claim 1, wherein the reactions are run in a closed system.

10. The process of claim 1, wherein step (a) is run with an alkane which is lower than a $C_{12}$ alkane.

11. The process of claim 1, wherein the oligomerization catalyst of step (b) comprises a nickel, platinum or palladium metal catalyst complex comprising the metal complexed with a nitrogen containing bi- or tridentate ligand.

12. The process of claim 11, wherein the metal catalyst complex of step (b) is of the formula $LMX(X')_n$, where n=0, 1 or 2;

X and X' are moieties into which a monomer can insert;

M is selected from the group consisting of nickel, platinum and palladium; and

L is a nitrogen containing bi- or tridentate ligand.

13. The process of claim 12, wherein L is a benzimidazolyl based ligand.

14. The process of claim 12, wherein X and X' are independently selected from the group consisting of halides, hydride, triflate, acetates, borates, $C_1$ through $C_{12}$ alky, $C_1$ through $C_{12}$ alkoxy, $C_3$ through $C_{12}$ cycloalkyl, $C_3$ through $C_{12}$ cycloalkoxy, $C_6$ through $C_{14}$ aryl, $C_7$ through $C_{17}$ aralkyl and olefins.

15. The process of claim 12, wherein L has the formula

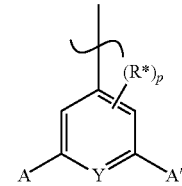

wherein A and A' are independently selected from the group consisting of:

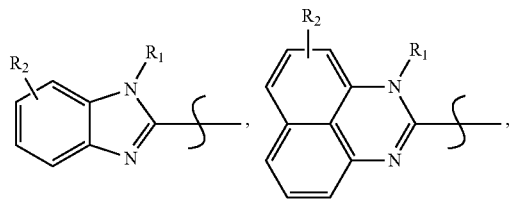

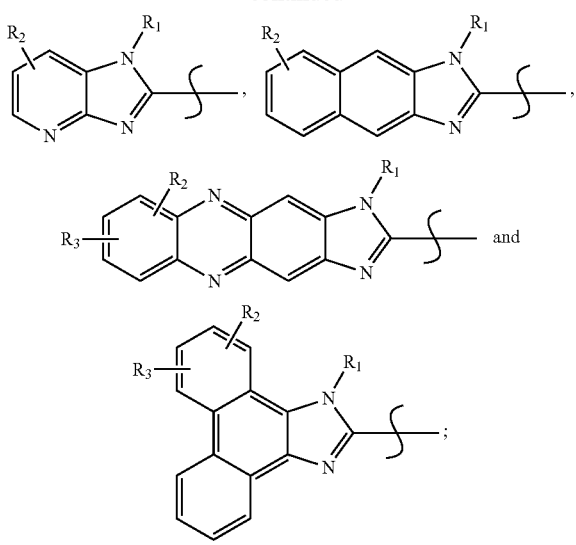

$R_1$, $R_2$, $R_3$ and R* are independently selected from the group consisting of halide, hydride, triflate, acetate, borate, $C_1$ through $C_{12}$ alky, $C_1$ through $C_{12}$ alkoxy, $C_3$ through $C_{12}$ cycloalkyl, $C_3$ through $C_{12}$ cycloalkoxy, $C_6$ through $C_{14}$ aryl, $C_7$ through $C_{17}$ aralkyl and olefins;

and Y is selected from the group consisting of C—H, C—Cl, C—Br, C—I, N, P, C—OR$_4$, wherein R$_4$ is hydrogen, an optionally substituted acyl group, a substituted or unsubstituted alkylsulfonyl group, or other leaving group; and p=0,1 or 2.

16. The process of claim 12, wherein the olefins of step (b) are contacted with a combination of the metal catalyst complex and a co-catalyst.

17. The process of claim 8, wherein the co-catalyst is selected from the group consisting of alkylalumoxanes, aluminum alkyls, aluminum halides, alkyl aluminum halides, Lewis acids, alkylating agents, and mixtures thereof.

18. The process of claim 17, wherein the co-catalyst is methyalumoxane.

19. The process of claim 1, wherein the reactions are conducted in a solvent.

20. The process of claim 1, wherein an iridium catalyst complex is the catalyst of step (a) and a metal catalyst complex is the catalyst of step (b), and the ligands of each catalyst complex are the same.

21. The process of claim 1, wherein the oligomerization catalyst is a nickel, platinum or palladium metal catalyst complex, and the ligands are the same as in the iridium catalyst complex.

22. The process of claim 21, wherein the ligands are benzimidazolyl-containing ligands.

23. The process of claim 1, wherein said alkane is selected from the group consisting of straight chain alkanes, branched chain alkanes and cycloalkanes.

24. The process of claim 23, wherein said alkane is a straight chain or branched chain alkane.

25. The process of claim 23, wherein the alkane is a cycloalkane.

* * * * *